US012725680B2

(12) United States Patent
Saeed et al.

(10) Patent No.: US 12,725,680 B2
(45) Date of Patent: Sep. 1, 2026

(54) SYSTEMS AND METHODS FOR PREDICTING PROPERTIES OF PEPTIDES DIRECTLY FROM MASS SPECTROMETRY DATA

(71) Applicants: Fahad Saeed, Miami, FL (US); Muhammad Usman Tariq, Miami, FL (US)

(72) Inventors: Fahad Saeed, Miami, FL (US); Muhammad Usman Tariq, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 19/058,586

(22) Filed: Feb. 20, 2025

(65) Prior Publication Data

US 2026/0245663 A1 Aug. 20, 2026

(51) Int. Cl.
*G16B 40/10* (2019.01)
*G06N 3/0442* (2023.01)

(52) U.S. Cl.
CPC .......... *G16B 40/10* (2019.02); *G06N 3/0442* (2023.01)

(58) Field of Classification Search
CPC .............................. G06N 3/0442; G16B 40/10
See application file for complete search history.

(56) References Cited

U.S. PATENT DOCUMENTS 11,251,031 B1 * 2/2022 Saeed .................... G16B 40/10
11,573,239 B2 * 2/2023 Shan ...................... G16B 50/20
11,862,298 B1 * 1/2024 Palaniappan .......... G16B 30/00
2022/0208540 A1 * 6/2022 Behsaz ................ G06N 3/0464
2022/0301659 A1 * 9/2022 Tang ..................... G06N 3/045

FOREIGN PATENT DOCUMENTS

WO WO-2024072802 A1 * 4/2024 ............... G06N 3/09
WO WO-2024073501 A1 * 4/2024 ............ G16B 25/10

OTHER PUBLICATIONS

Jørgensen, Philip JH, et al. "Probabilistic parafac2." Entropy 26.8 (Year: 2024).*
J0rgensen, Philip JH, et al. "Probabilistic parafac2." Entropy 26.8 (Year: 2024).*
Hansson, Karl. "Cerebrospinal fluid peptidomics: discovery of endogenous peptides as biomarkers of Alzheimer's disease." (Year: 2018).*

* cited by examiner

*Primary Examiner* — Adam C Standke
(74) *Attorney, Agent, or Firm* — SALIWANCHIK, LLOYD & EISENSCHENK

(57) ABSTRACT

Systems and methods are provided for predicting properties of peptides directly from mass spectrometry (MS) data. Machine learning (ML) models can be used to predict properties of the peptides, before any deduction, directly from MS data. Systems and methods are also provided for quantifying the confidence of the inference of the ML models, and these metrics can be specific to the MS-based omics data sets.

17 Claims, 14 Drawing Sheets

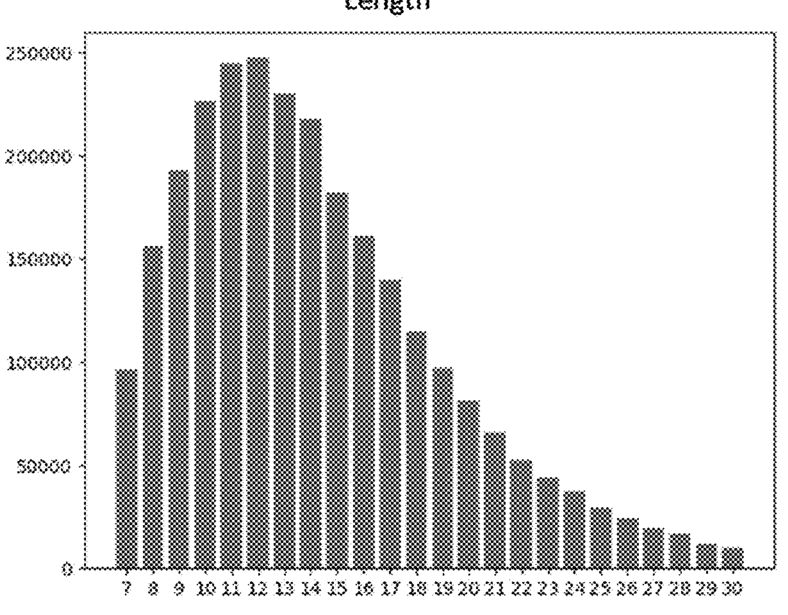
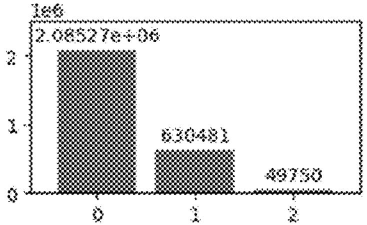
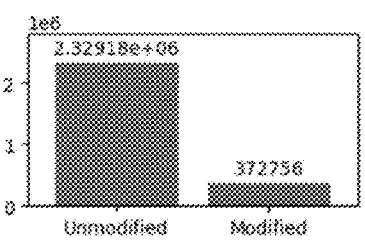
FIG. 8

| Score Type | Variations | Density | Consistency | Variations + Density | Variation + Consistency | Density + Consistency | Variation + Density + Consistency |
|---|---|---|---|---|---|---|---|
| ROC-AUC | 0.84 | 0.74 | 0.72 | 0.88 | 0.84 | 0.83 | 0.92 |
| F1 Score | 0.77 | 0.68 | 0.67 | 0.80 | 0.74 | 0.76 | 0.87 |
| Precision | 0.75 | 0.66 | 0.65 | 0.79 | 0.81 | 0.78 | 0.85 |
| Recall | 0.79 | 0.70 | 0.69 | 0.81 | 0.68 | 0.74 | 0.88 |

FIG. 10

| Score Type | Variations | Density | Consistency | Variations + Density | Variation + Consistency | Density + Consistency | Variation + Density + Consistency |
|---|---|---|---|---|---|---|---|
| ROC-AUC | 0.98 | 0.85 | 0.59 | 0.91 | 0.99 | 0.98 | 0.99 |
| F1 Score | 0.96 | 0.78 | 0.56 | 0.84 | 0.97 | 0.96 | 0.99 |
| Precision | 0.95 | 0.80 | 0.55 | 0.83 | 0.97 | 0.97 | 0.99 |
| Recall | 0.96 | 0.71 | 0.57 | 0.85 | 0.97 | 0.96 | 0.99 |

FIG. 11

| Hyper Parameter | Value |
|---|---|
| Max Depth | 30 |
| Min Samples_split | 2 |
| No. of Estimators | 200 |

FIG. 12

| Hyper Parameter | Value |
|---|---|
| Max Depth | 5 |
| Min Samples_split | 2 |
| No. of Estimators | 200 |

FIG. 13

SYSTEMS AND METHODS FOR PREDICTING PROPERTIES OF PEPTIDES DIRECTLY FROM MASS SPECTROMETRY DATA

GOVERNMENT SUPPORT

This invention was made with government support under Award Number R35 GM153434 awarded by the National Institutes of Health. The government has certain rights in the invention.

BACKGROUND

Database search algorithms reduce the number of potential candidate peptides against which scoring needs to be performed using a single property (i.e., mass) for filtering. While useful, filtering based on one property can lead to exclusion of non-abundant spectra and uncharacterized peptides, potentially exacerbating the streetlight effect.

BRIEF SUMMARY

Embodiments of the subject invention provide novel and advantageous systems and methods for predicting properties of peptides directly from mass spectrometry (MS) data. Machine learning (ML) models can be used to predict properties of the peptides, before any deduction, directly from MS data. Embodiments also provide systems and methods for quantifying the confidence of the inference of the ML models, and these metrics can be specific to the MS-based omics data sets.

In an embodiment, a system for predicting properties of peptides from MS data of the peptides can comprise: a processor; and a machine-readable medium in operable communication with the processor and having instructions stored thereon that, when executed by the processor, perform the following steps: i) receiving the MS data as input; ii) capturing sequence dependencies in the MS data; iii) generating an intermediate output using the sequence dependencies; iv) combining a feature vector of mass and charge values with the intermediate output to generate a combined feature vector; v) generating spectrum embeddings using the combined feature vector; and vi) predicting the properties of the peptides based on the spectrum embeddings. The properties of the peptides can be predicted directly from the MS data without any prior deduction or database search on the MS data. The MS data can comprise mass to charge ratio (m/z), intensity, and/or index value. The properties of the peptides can comprise length, missed cleavages, and/or modification status. The capturing of the sequence dependencies in the MS data can comprise using two 8-headed self-attention layers. The predicting the properties of the peptides based on the spectrum embeddings can comprise sending the spectrum embeddings through a first branch of two fully connected layers to predict a first property of the peptides, a second branch of two fully connected layers to predict a second property of the peptides, and a third branch of two fully connected layers to predict a third property of the peptides. The generating of an intermediate output using the sequence dependencies can comprise sending the sequence dependencies through two fully connected layers to generate the intermediate output. The instructions when executed can further perform any or all of the following steps: vii) determining a certainty of embedding location by introducing controlled augmentations to the MS data and measuring a variation in the spectrum embeddings; viii) measuring a training data density around spectrum embedding using a von Mises-Fisher Mixture Model; and/or ix) evaluating whether a first density of the MS data is consistent with a second density of the spectrum embeddings. The system can further comprise a display in operable communication with the processor and/or the machine-readable medium. The instructions when executed can further perform any or all of the following steps: displaying the predicted properties of the peptides on the display (and/or the results of any of intermediate steps i)-v)) and/or displaying the results of any or all of steps vii), viii), and ix) (if performed) on the display. The instructions when executed can further perform any of all of the following steps: providing (e.g., to a scientist, a clinician, and/or a health care professional) at least one new filter for database search of peptides, based on the predicted peptide properties; providing (e.g., to a scientist, a clinician, and/or a health care professional) the predicted peptide properties for use in clinical proteomics; and/or using (e.g., by a scientist, a clinician, and/or a health care professional) the predicted peptide properties in clinical proteomics.

In another embodiment, a method for predicting properties of peptides from MS data of the peptides can comprise: i) receiving (e.g., by a processor) the MS data as input; ii) capturing (e.g., by the processor) sequence dependencies in the MS data; iii) generating (e.g., by the processor) an intermediate output using the sequence dependencies; iv) combining (e.g., by the processor) a feature vector of mass and charge values with the intermediate output to generate a combined feature vector; v) generating (e.g., by the processor) spectrum embeddings using the combined feature vector; and vi) predicting (e.g., by the processor) the properties of the peptides based on the spectrum embeddings. The properties of the peptides can be predicted directly from the MS data without any prior deduction or database search on the MS data. The MS data can comprise mass to charge ratio (m/z), intensity, and/or index value. The properties of the peptides can comprise length, missed cleavages, and/or modification status. The capturing of the sequence dependencies in the MS data can comprise using (e.g., by the processor) two 8-headed self-attention layers. The predicting the properties of the peptides based on the spectrum embeddings can comprise sending (e.g., by the processor) the spectrum embeddings through a first branch of two fully connected layers to predict a first property of the peptides, a second branch of two fully connected layers to predict a second property of the peptides, and a third branch of two fully connected layers to predict a third property of the peptides. The generating of an intermediate output using the sequence dependencies can comprise sending (e.g., by the processor) the sequence dependencies through two fully connected layers to generate the intermediate output. The method can further comprise any or all of the following steps: vii) determining (e.g., by the processor) a certainty of embedding location by introducing controlled augmentations to the MS data and measuring a variation in the spectrum embeddings; viii) measuring (e.g., by the processor) a training data density around spectrum embedding using a von Mises-Fisher Mixture Model; and/or ix) evaluating (e.g., by the processor) whether a first density of the MS data is consistent with a second density of the spectrum embeddings. The system can further comprise a display in operable communication with the processor and/or the machine-readable medium. The method can further comprise any or all of the following steps: displaying (e.g., by a display in operable communication with the processor) the predicted properties of the peptides (and/or the results of any of intermediate steps i)-v)) and/or displaying (e.g., by the display) the results of any or all of steps vii), viii), and ix) (if performed). The method can further comprise any of all of the following steps: providing (e.g., to a scientist, a clinician, and/or a health care professional) at least one new filter for database search of peptides, based on the predicted peptide properties; performing (e.g., by a scientist, a clinician, and/or a health care professional) a database search using the new filter(s); providing (e.g., to a scientist, a clinician, and/or a health care professional) the predicted peptide properties for use in clinical proteomics; using (e.g., by a scientist, a clinician, and/or a health care professional) the predicted peptide properties in clinical proteomics; and/ or diagnosing (e.g., by a scientist, a clinician, and/or a health care professional) at least one disease (that can specifically be diagnosed on the basis of proteomics and/or peptide properties) using the predicted peptide properties.

BRIEF DESCRIPTION OF DRAWINGS

FIG. 4 shows that the in-distribution data points can be predicted with all degree of accuracy with all different data sets.

FIG. 8 shows a distribution of peptide length, missed-cleavages, and modifications of training data. The distribution of larger length spectra were fewer in number. In order to overcome this, oversampling can be done from larger length examples inversely proportional to the count. Similar to length distribution, the examples from 1 and 2 missed cleavages, and examples from modified peptides, can be oversampled for balancing the training data.

FIG. 10 shows a table of performance of uncertainty metrics on retrieving high-quality examples from in-distribution data. The values indicate that combining multiple metrics improves the ability to detect high-quality examples significantly with the area under the receiver operating characteristic curve (ROC-AUC) value of 0.94.

FIG. 11 shows a table of performance of uncertainty metrics on retrieving in-distribution data from a mix of in-distribution and out-of-distribution examples. The values indicate that density consistency is the major contributor towards distinguishing between the two classes with an ROC-AUC of 0.99.

FIG. 12 shows a table of optimal hyperparameters values for a gradient-boosting decision tree (GBDT) model.

FIG. 13 shows a table of optimal GBDT hyperparameters value for epistemic uncertainty.

DETAILED DESCRIPTION

Figure 1:
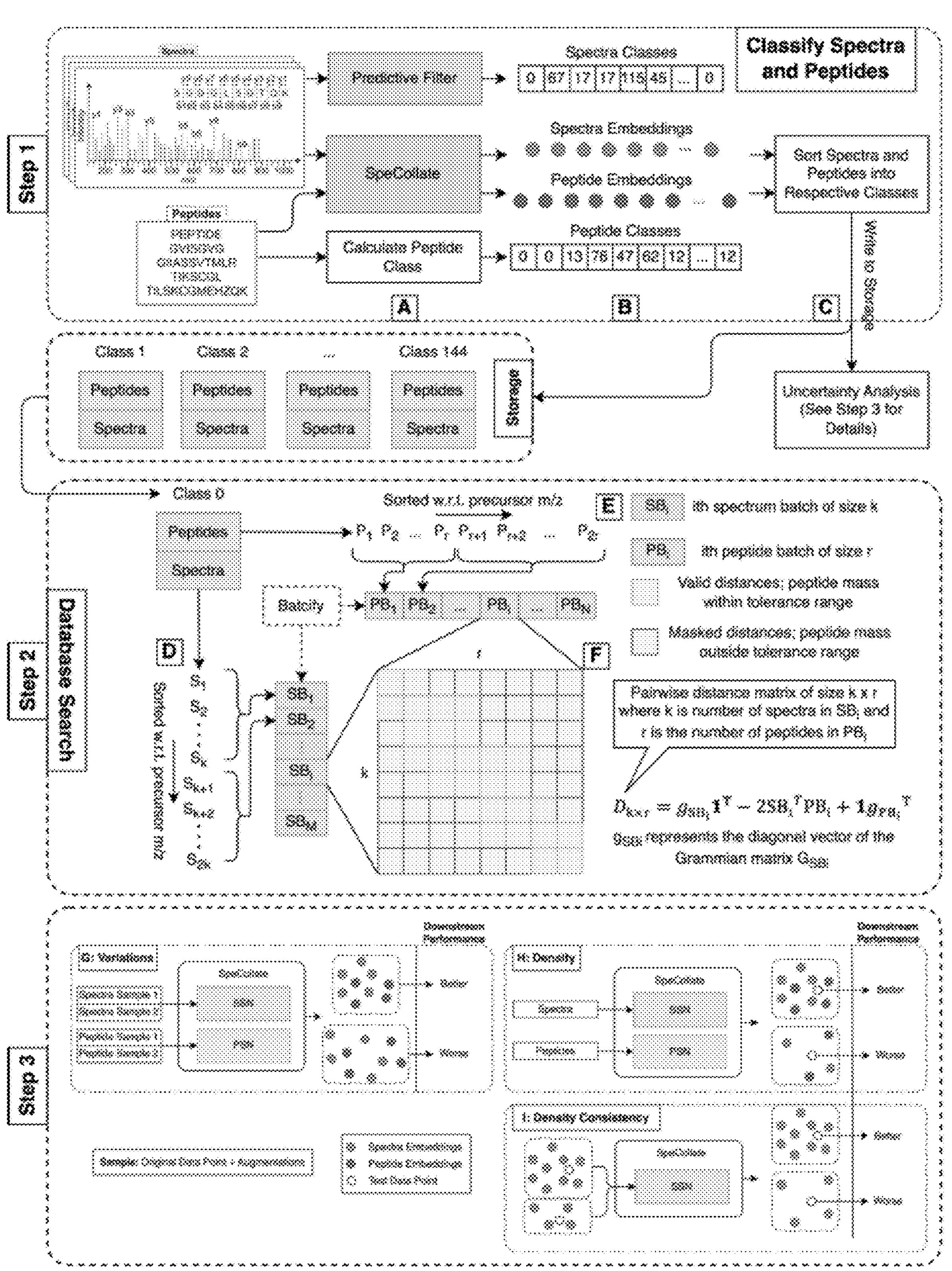
FIG. 1 shows a schematic view of a filtered meta proteomics database search pipeline, according to an embodiment of the subject invention. In Step 1(A), spectra and peptide embeddings can be generated (e.g., using SpeCollate) while the predictive model assigns a class (e.g., out of 144) for each spectrum. In Step 1(B), the class for a peptide can be calculated from the amino acid sequence. In Step 1(C), spectra-peptide classes can be stored. In Step 2(D,E), spectra and peptides can be batched to fit them in server memory. In Step 2(F), the distance matrix of spectra and peptide embeddings in a given batch can be calculated. In Step 3(G), per-feature sample variations and their correlation with downstream performance can be shown. A sample, the original data point plus augmentation, has lower feature variations when the middle is generally more confident about the original data point. In Step 3(H), the density of training data around a given test data point indicates higher model confidence and hence improved downstream performance. In Step 3(I), density consistency can measure how consistent the input data density is with the embedding density. This feature is important in estimating how well the model is able to capture the data structure and relations.

Embodiments of the subject invention provide novel and advantageous systems and methods for predicting properties of peptides directly from mass spectrometry (MS) data. Machine learning (ML) models can be used to predict properties of the peptides, before any deduction, directly from MS data. Embodiments also provide systems and methods for quantifying the confidence of the inference of the ML models, and these metrics can be specific to the MS-based omics data sets. Predicting the properties of peptides can lead to improvement in the current pipelines for peptide deduction, while also providing more scalable workflows for peptide deduction search-engines. Quantifying the uncertainty metrics can provide a better understanding of the inferences by the ML models, allowing users (e.g., scientists) to understand how confident the search engine is for the given peptide(s) (especially if it is new).

Systems and methods of embodiments of the subject invention (which can be referred to herein as "ProteoRift") provide a novel attention and multitask deep network, which can predict multiple peptide properties (e.g., length, missed cleavages, and/or modification status) directly from (MS) spectra. ProteoRift can predict these properties with very high accuracy (e.g., at least 90%, such as at least 95% or at least 97%), resulting in high search-space reduction (e.g., a reduction of at least 75%, at least 80%, at least 85%, or at least 90%). As a result, the end-to-end pipeline can have speedups (e.g., at least 5×, at least 8×, at least 9×, at least 10×, at least 11×, at least 12×, or in a range of from 5× to 20×, such as 8× to 12× speedups) with peptide deduction accuracy comparable to algorithmic techniques. Two uncertainty estimation metrics can also be formulated and can distinguish between in-distribution and out-of-distribution data (area under the receiver operating characteristic curve (ROC-AUC) of 0.99) and predict high-scoring mass spectra against correct peptide (ROC-AUC of 0.94). These models and metrics can be integrated in an end-to-end ML pipeline.

Reduction in search-space using peptide mass as a filter is one of the most fundamental techniques utilized to make database-search algorithms scalable. While mass is just one property of spectra and associated peptide, filtering does reduce unnecessary comparisons, minimizes the high-scoring miss-matches, and improves the search accuracy. However, related art algorithms using precursor and fragment ion masses were not designed to handle the complexity of multiple non-model biological entities, such as meta-proteomics investigations. The continuous nature of the mass filter, when used for meta-proteomics data analysis, leads to either a large number of false positive peptides expelled from further analysis or unreasonable search times because of very large and redundant databases, or both. The MS community is aware of unidentified peptides that do not get "matched" even when in the database, resulting in the development of "open-search" and "hybrid-search" mechanisms. In "open-search" methods, the mass filter is increased significantly, resulting in large number of candidate peptides included in the scoring that would otherwise get missed. Methods such as MSFragger have improved on the identification of the peptides, but execution of search-space restriction remain fundamentally the same (i.e., mass of the spectra and corresponding peptides) (see also Kong et al., Msfragger: ultrafast and comprehensive peptide identification in mass spectrometry-based proteomics, Nature methods, 14(5):513-520, 2017; which is hereby incorporated by reference herein in its entirety). However, among other factors, a combination of technological limitations has resulted in inaccuracies including misidentification/no-identification of peptides, inconsistencies between search engines, and a tendency to identify abundant peptides leading to the street-light effect (see also Kustatscher et al., Understudied proteins: opportunities and challenges for functional proteomics, Nature Methods, 19(7):774-779, July 2022; which is hereby incorporated by reference herein in its entirety).

Figure 6:
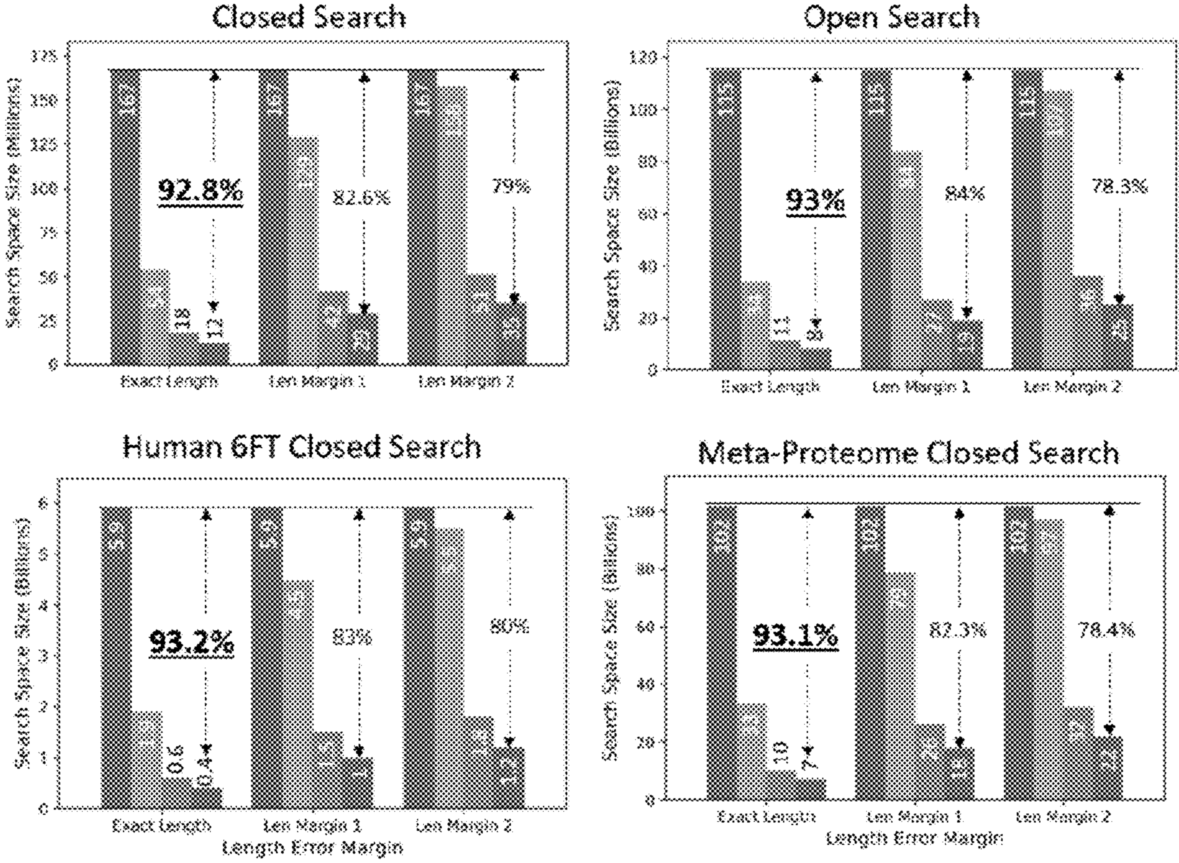
FIG. 6 shows plots of search space size (in billions) versus length error margin for closed search (upper left), open search (upper right), human 6FT closed search (bottom left), and meta-proteome closed search (bottom right). In each data grouping, the left-most bar is for no filter, the second-from-the-left bar is for only lens, the second-from-the-right bar is for Len+Cleavs, and the right-most bar is for Len+Cleavs+Mods. The analysis to give these results shows that accurately predicting the length, missed cleavages, and modification status can significantly reduce the search space size and provide database search speedup by reducing the number of redundant matches that need to be performed normally. This analysis was performed for human databases. Three different sets of experiments were performed for different length error tolerances. The speedup gain from the length filter was minimal when allowing error tolerance of more than ±1.

Routine usage of ML models remains challenging because ML scoring functions are inserted in the "algorithmic" workflow, resulting in peptides similar to their algorithmic counterparts. Embodiments of the subject invention provide deep learning models that can predict peptide features (e.g., peptide length, missed cleavages, and/or modifications) directly from spectra embedding (i.e., before any database search). The network input(s) can include mass to charge ratio (m/z), intensity, and/or index values of spectra using the attention network. These can incorporate precursor mass and charge value of the spectrum to predict all the features simultaneously using the multitasking technique. Theoretical analysis shows that successfully applying filters reduces the search space size by more than 90% (see FIG. 6), which has also been demonstrated with experiments using real-world data (see FIGS. 3A-3D). The extensive experimentation with open data demonstrates that the models of embodiments can predict peptide lengths (e.g., by 92% precision or more), missed cleavages (e.g., by 95% precision or more), and modifications status (e.g., by 97% precision or more).

In some embodiments, the ML model Specollate can be retrained by incorporating newly designed filters in the ML workflow (see also, Tariq and Saeed, Specollate: Deep cross-modal similarity network for mass spectrometry data based peptide deductions, PloS one, 16(10):e0259349, 2021; which is hereby incorporated by reference herein in its entirety). These ML filtering models when integrated with a database search engine can lead to a considerable speedup (e.g., 8× to 12× speedup) while maintaining peptide accuracies at par with highly successful related art search engines such as Crux and MSFragger. In addition, MS-specific metrics have been developed to quantify the uncertainty associated with spectra embeddings, and their inferred peptides using the re-trained SpeCollate model. The results demonstrate that the metrics can distinguish in-distribution and out-of-distribution data (ROC-AUC of 0.99) and predict high-scoring mass spectra against the correct peptide (ROC-AUC of 0.94). These measures provide insight into the model's stability, confidence, and data representation ability, aiming to empower confident usage of ML tools in systems biology settings.

ProteoRift is a deep attention-based multitask network that enables prediction of peptide properties directly from the spectra (e.g., MS). FIG. 1 shows an end-to-end database search pipeline, according to an embodiment of the subject invention, which enables comparison of results directly to traditional algorithms such as Tide and MSFragger. Different stages of ML end-to-end pipeline for peptide deduction were designed and developed (see also FIG. 1). In the first step, an attention-based network can generate spectra and peptide embeddings. Thereafter, a multi-task network can be used to predict peptide-length, missed cleavages, and modifications status directly from spectra before any peptide deduction. The second step can include binning spectra and peptides using the predictions from the first step. These batches can then be used for performing database search for peptide deduction using spectra and peptide in a single batch (i.e., no intra-batch-deductions are performed). Provided that the first step resulted in a correct prediction, the peptides and the spectra that are supposed to match would be in the same batches. The third step can include developing (novel) metrics to quantify the uncertainty associated with spectra embeddings and peptide deduction. These confidence metrics can be reported back with the results of the spectra-to-peptide matches. This complete end-to-end ML pipeline can then be used for all experimentation as well as comparison with existing methods. This is the first end-to-end ML pipeline that predicts peptide properties directly from the spectra, and enables more scalable, accurate, and trustworthy peptide deductions.

The utility of database-search ML models might be subject to various degrees of vagueness influenced by multifaceted factors. This imprecision encapsulates two key dimensions: aleatoric; and epistemic (see also Der Kiureghian and Ditlevsen, Aleatory or epistemic? does it matter? Structural safety, 31(2):105-112, 528 2009; which is hereby incorporated by reference herein in its entirety). Aleatoric imprecision originates from the inherent noise and stochasticity in the data, whereas epistemic imprecision mirrors the model's limitations, signifying the unlearned or unknown aspects within the model's purview. Such uncertainty estimation enables the reliability of the model's predictions. For example, elevated uncertainty in peptide or spectrum embeddings may signal model ambiguity in their representations, potentially indicating a misaligned peptide-spectrum match. Further, such uncertainty quantification provides insights into embedding areas that can be improved either by further training or acquiring more quality or diverse data. For example, higher epistemic uncertainty can indicate regions in the input space where the model is under-confident due to a lack of sufficient data. This can point out opportunities for further data collection or model improvement. Similarly, higher aleatoric uncertainty can point out the need for higher-quality data or preprocessing for noise removal. Most importantly, uncertainty estimation allows for risk-aware decision-making. In high-stakes applications such as clinical proteomics, where incorrect peptide identification could lead to misleading conclusions, being aware of the uncertainty associated with each prediction can help avoid potentially costly or harmful decisions.

Embodiments of the subject invention can include uncertainty metrics that can be used to assess the confidence in the peptide deduction (i.e., how confident the user (e.g., a scientist) should be in the inference especially when the identified peptide is novel). The aleatoric and epistemic uncertainty of SpeCollate's embeddings can be estimated using the proposed metrics, and it can be analyzed how they can inform about the model's performance and its output confidence. To this end, three different metrics for estimating the uncertainty of the embeddings can be considered. First, the certainty of embedding location can be assessed by introducing controlled augmentations to the input spectra and then measuring the variation in the output embeddings. Second, the density of the training data around each embedding can be measured using a von Mises-Fisher (vMF) Mixture Model to determine how much data the model has seen around a given data point. Third, it can be evaluated whether the density is consistent between the input spectra and their embeddings, indicating whether the model can maintain data structure and relationships.

ProteoRift is an ML model that can predict multiple peptide properties (length, missed cleavages, and modification status) directly from spectra. These properties when used for search-space reduction, result in superior speeds (e.g., 8× to 12× faster) and comparable results for both proteomics, and meta-proteomics experiments (see the Examples below). Given that different properties of peptides and the spectra can be used for search-space reduction, the usage of mass-only filtering by existing methodologies is a bottleneck, especially for searches that involve proteogenomics, meta-proteomics or non-model organisms. Certainty metrics can be used to enable confidence estimation of the results, especially for identification of novel and uncommon peptides, potentially reducing the skepticism of results obtained using black-box ML models.

ProteoRift is a prune-and-search method that can result in reduction in accuracy with successive pruning attempts.

Accumulation of more filtering decreases the search-space, and results in decreased false-positives. However, this also results in a decrease in the number of identified peptides due to summation of the errors by three different heads. This model prediction error can be attributed to the imbalance in data (see also FIG. 8), where the distribution of features is highly skewed and some labels have very few training examples. ProteoRift is a supervised learning technique, and the amount of labeled data available is one of the limitations of the method. Therefore, the accuracy of the peptide properties achieved using ProteoRift, and subsequent peptides deduced, are limited by labeled data that is currently in short supply.

Embodiments of the subject invention provide deep attention-based multitask networks (ProteoRift). Embodiments provide: an attention-based network to generate spectra and peptide embeddings; a multi-task network to predict peptide-length, missed cleavages, and modifications status directly from spectra; novel metrics to quantify the uncertainty associated with spectra embeddings; and predictive filtering based peptide database search that takes into account the confidence of spectra embeddings.

Figure 5:
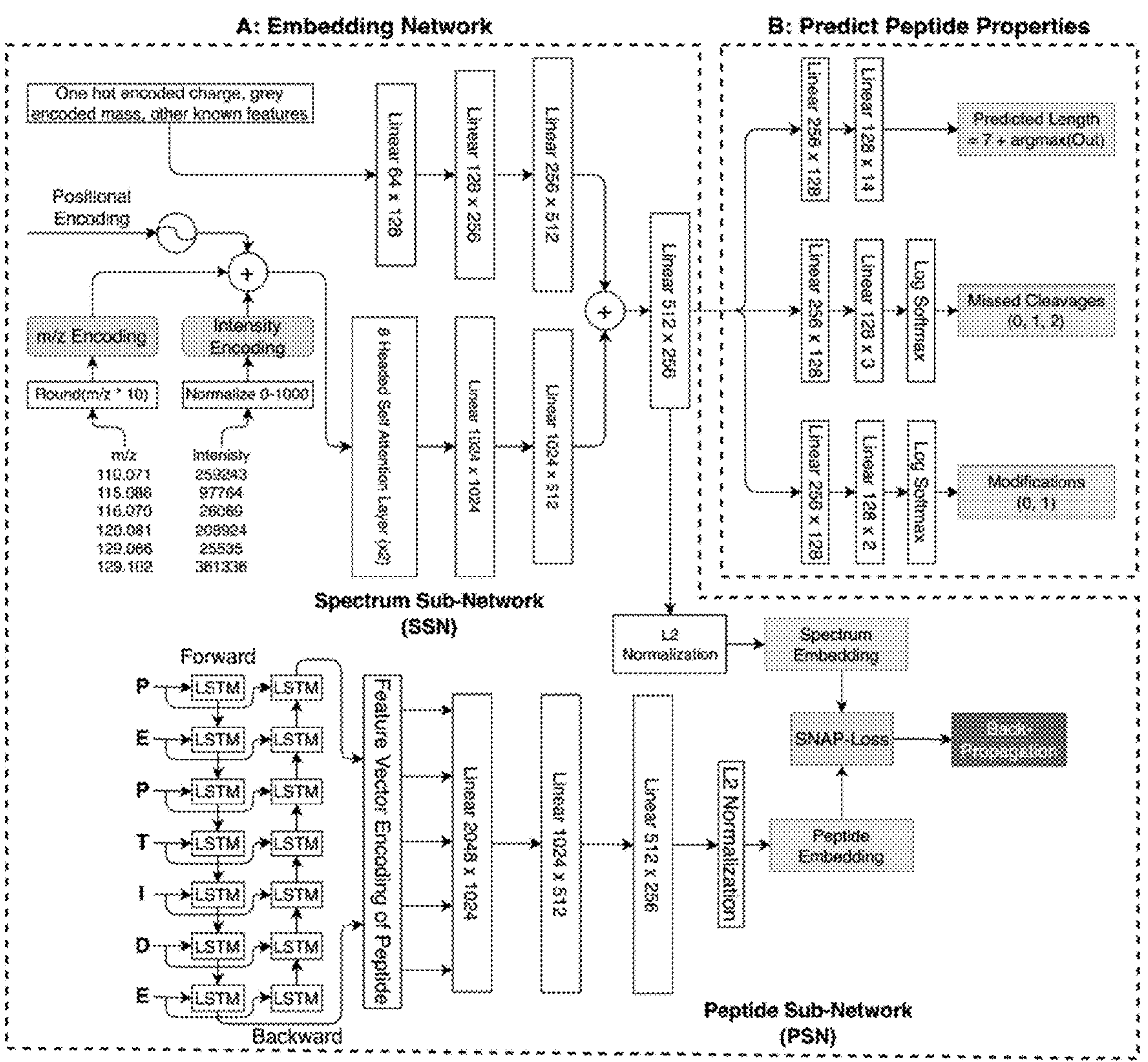
FIG. 5 shows a schematic view of the network architecture for generating spectra and peptide embeddings, according to an embodiment of the subject invention. In spectral sub-network (SSN), spectra m/z and intensity values can be treated as two separate sequences and embedded using separate embedding layers. Sinusoidal positional encoding can also be added to the embeddings to maintain sequence order information. An intermediate spectrum feature vector can be added with charge and mass feature vectors and passed through a fully connected layer (e.g., a fully connected layer of 512×256). In peptide sub-network (PSN), peptide embeddings can be generated using two bidirectional long short-term memory (BiLSTM) layers followed by three fully connected layers. From the spectrum embeddings, three branches of fully connected layers can predict the peptide length, missed cleavages, and/or modifications (as shown in the section with dotted lines marked as "B" in FIG. 5). All the output branches can calculate loss separately using the LogSoftmax function, and a weighted sum of three losses can be calculated before calculating gradients.
Figure 7:
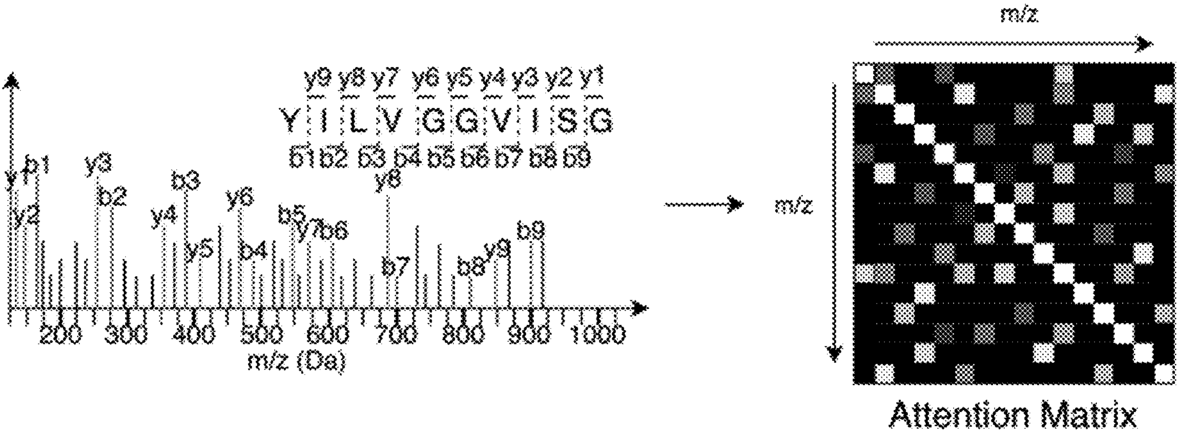
FIG. 7 shows a spectrum and an attention matrix, showing that the attention mechanism is useful in capturing long distance as well as short distance relation within a spectrum and allows for more meaningful feature extractions.

ProteoRift is an ML model to predict peptide properties directly from the MS spectra. A first challenge is to translate spectra and peptides' high-dimensional sparse vectors into embeddings that can place semantically similar spectra and peptide inputs close together in the embedding space. An embedding network, as shown in FIG. 5, can be used. The network can use self-attention layers to embed mass spectra. Using self-attention layers for embedding mass spectra is useful in capturing long-distance relations between peaks (e.g., complimentary b and y peaks as well as short-distance relations (e.g., a neutral loss or isotopic peak)) (see also FIG. 7). For successfully capturing all the information in the spectrum, m/z, and intensity sequences are first discretized (i.e., m/z values are binned in 0.1 Dalton (Da)-sized bins), and intensity values are discretized between 0-1000 before passing them through the embedding layers. Because attention layers process the entire sequence at the same time, the sequence information needs to be encoded separately. For this purpose, sinusoidal harmonics can be used (see also, Vaswani et al., Attention is all you need, Advances in neural information processing systems, 30, 2017; which is hereby incorporated by reference herein in its entirety). The m/z and intensity embedding, as well as the sequence encoding, are of the same size and are added together before being processed by the attention layer.

Next, sixteen-headed attention layers can be used to capture the sequence dependencies in the spectrum. The attention layers can be followed by two fully connected layers (e.g., of size 2048×1024 and 1024×512). The feature vector of mass and charge values can be added to the intermediate output after the second fully connected layer. The combined feature vector can be passed through another fully connected layer to generate spectrum embedding (e.g., of length 256).

Peptide embedding can be generated using two bidirectional long short-term memory (Bi-LSTM) networks. Amino acid level embedding can be generated using an embedding layer, and can be fed to the Bi-LSTM, which can generate output vectors (e.g., of size 2048 per peptide). Only the final amino acid output is kept and fed to the following layers. Next, two fully connected layers (e.g., of size 1024, 512, and 256) can be used. The final layer can be preceded by L2 normalization to generate normalized vectors (e.g., of length 256 for each peptide).

From the spectrum embeddings, three branches of fully connected layers predict the peptide length, missed cleavages, and modifications, as shown in FIG. 5 (section labeled "B"). For the length prediction, the two fully connected layers (e.g., of 256×128 and 128×24) can be used. The output layers are of length 24 because lengths from 7-30 AAs can be predicted. The missed cleavage branch can contain two fully connected layers (e.g., of size 256×128 and 128×3) as only a max of two missed cleavages may be considered. Finally, the modification branch can include two fully connected layers (e.g., of size 256×128 and 128×2). It can be predicted whether the spectrum is modified or not. The exact number of modifications can also be predicted, as well as the specific known modifications that exist in the spectrum. All the output branches calculate loss separately using the LogSoftmax function, and a weighted sum of three losses is calculated before calculating gradients.

Figure 9:
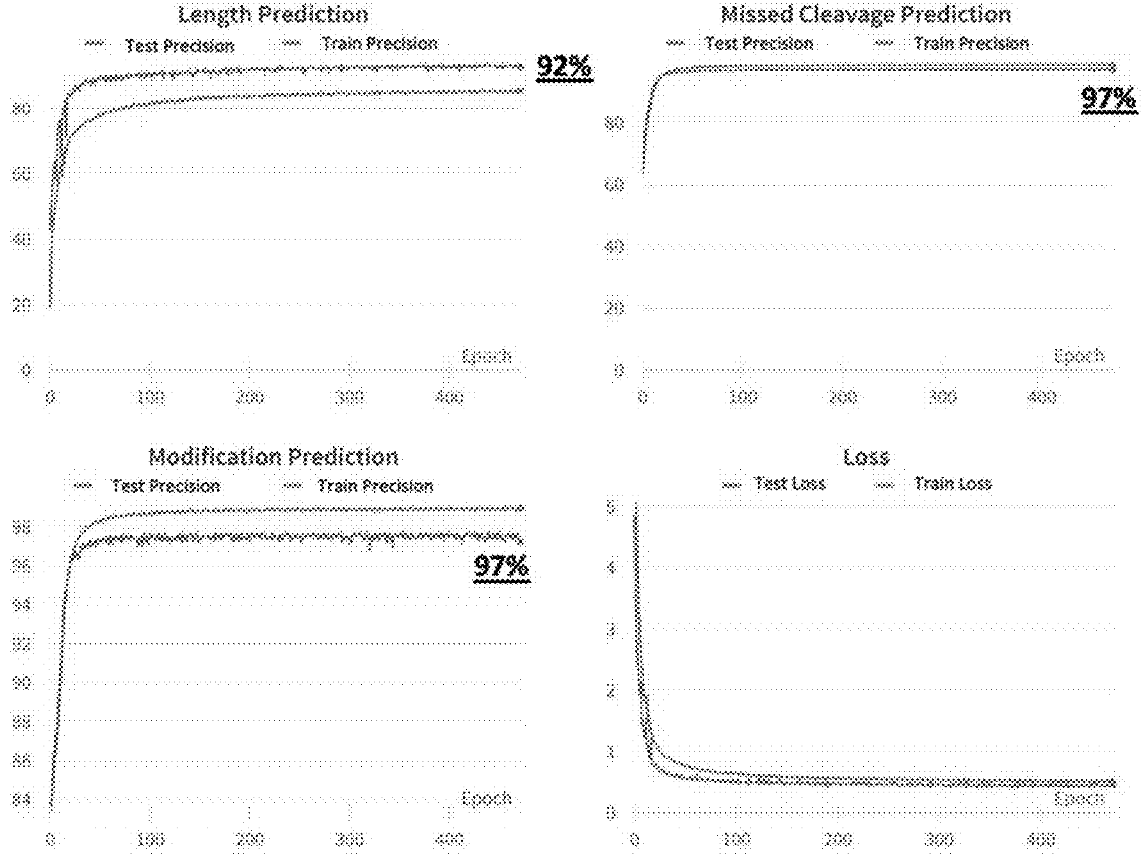
FIG. 9 shows training plots for length prediction (top left), missed cleavage prediction (top right), modification prediction (bottom left), and loss (bottom right). These plots show that a network was trained for 500 epochs to achieve the test performance of 92% for peptide length, 97% for missed cleavages, and 97% for the status of the modifications.

The training process can begin with a forward pass of the batch containing encoded spectra. Three sets of labels can be used (i.e., peptide length, missed cleavages, and modifications status). The network can generate three separate outputs for each feature, respectively, which can be treated as multi-class classification. The cross-entropy loss function can be applied to each feature separately to calculate three loss values. Before the backpropagation is performed, a weighted sum of the three losses can be calculated where the weights are determined through a randomized search. Adam optimizer can be used for gradient updates with a learning rate of 0.0001 and weight decay of 0.00005. A dropout of 0.3 can be used after the attention, and the fully connected layers during the training step. The dropout layers can be disabled during the evaluation step. The network trained for 500 epochs achieved 92% peptide length precision, 97% missed cleavage precision, and 97% modification precision, as shown in FIG. 9.

In order to implement the database search with the new filters, the database peptides and the experimental spectra were first pre-assigned into one of the 144 (7-30 peptide length×0, 1, or 2 missed cleavages×2 modifications statuses) classes based on their features (predicted from the ML filter). For the database peptides, the features are known and hence each peptide gets classified into a non-overlapping class. Spectra can be classified based on their predicted features using the ProteoRift model. A spectrum from a given class only gets searched against peptides in the same class. Because each class is non-overlapping, 144 parallel searches can be performed simultaneously. The general filtered database search flow is shown in FIG. 1, Step 2.

In the first step, spectra and peptides can be indexed into their respective classes based on their properties. Each spectrum and peptide can get assigned to a unique class. Spectra and peptides within each class can be batched. As shown in FIG. 1, Step 2, spectra in a given class (e.g., 7-1-0 (peptide length: 7, 1 missed cleavage, unmodified)) can be sorted with respect to the precursor mass, and split into batches (SB) (e.g., of size 1024). Similarly, peptides can be sorted with respect to their precursor mass, and candidate peptide lists can be generated for each SB. To generate a peptide list for a given SB, peptides in the mass range [MinSB−PreTol: MaxSB+PreTol] can be obtained. Here, MinSB and MaxSB are the minimum and maximum precursor masses in a given SB, respectively. PreTol is the user-specified precursor tolerance configuration. Next, each peptide list is split into batches (PB) (e.g., of 1024 peptides). The size can be adjusted according to the available memory. For each PB in a peptide list, a distance matrix against the SB is calculated. A mask is calculated for each spectrum where peptides outside the mass filter range are ignored. Next, the values in the distance matrix are sorted for each spectrum in increasing order of L2 distance, and k smallest distance peptides are kept for each spectrum as these are the highest-scoring peptides. The inverse of the L2 distance is reported as the match score. The process is repeated for each SB and results are written to a percolator input (pin) file (see also Kall et al., Semi-supervised learning for peptide identification from shotgun proteomics datasets, Nature methods, 4(11):923-925, 2007; which is hereby incorporated by reference herein in its entirety). A similar process is repeated for the decoy database for FDR analysis.

The incorporation of augmentation techniques to estimate the sample variance is a method employed to quantify the level of certainty a model has regarding the position of its predicted embedding. The principle lies in the deliberate modification of each data point in multiple ways (e.g. random omission of a certain percentage of peaks or adjusting the charges associated with spectra). Sample feature variation is shown in FIG. 1, Step 3 (part G).

Given an original spectrum s, n augmentations can be induced, thereby creating a set of altered spectra denoted by $\{s_1, s_2, \ldots, s_n\}$. Each derived spectrum embedding is a 256-dimensional vector. The variance, a statistical measure of the extent to which the data points deviate from their expected values is computed for each of these dimensions.

Mathematically, the sample variance a can be defined as follows:

$$\sigma = \frac{1}{n-1}\sum_{i=1}^{256}\sum_{j=1}^{n}(s_j[i]-\mu_i)^2$$

where $s_j$ [i] denotes the i-th element in the j-th augmentation, $\mu_i$ is the mean of the elements for the i-th dimension, and n is the number of augmentations.

To compile these individual variances into a single value, a cumulative sum is calculated across all dimensions. This total sum, or sample variance, is indicative of the model's confidence in the location of the predicted embedding; a smaller variance suggests a higher degree of certainty. In essence, this technique provides valuable insights into the model's confidence in its predictions, which can be crucial in the interpretation of the downstream performance. Only a trained model is required to estimate the variance.

The density of the embedding space around a spectrum embedding is the measure of how many training examples the model has seen close for a given example. The von Mises-Fisher distribution can be used to estimate the density of the embedding space around a given data point. As the spectra and peptide embeddings generated by SpeCollate are L2-normalized, the von Mises-Fisher distribution, particularly when combined into a mixture model (vMFMM), is an ideal choice for modeling data due to its directional properties. Density estimation is visualized in FIG. 1, Step 3 (part H).

Assuming a set of N training examples $\{s_1, s_2, \ldots, s_N\}$ and assuming these are normalized to unit length; fit a vMFMM to this data with K components. Each component k has a center $\mu_k$ and a concentration parameter $\kappa_k$ and a weight $w_k$. The density p(s) for any point s in this mixture model can be computed as:

$$p(s) = \sum_{k=1}^{K} w_k \cdot p_k(s)$$

where $p_k(s)$ is the probability density of spectrum embedding s in the k-th von Mises-Fisher component, defined as:

$$p_k(s) = C_m(\kappa_k) \cdot e^{\kappa_k \cdot \mu_k^T x}$$

where $C_m(\kappa)$ is the normalization constant in m dimensions, given by:

$$C_m(\kappa) = \frac{\kappa^{\frac{m}{2}-1}}{(2\pi)^{\frac{m}{2}} I_{\frac{m}{2}-1}(\kappa)}$$

where $I_{m/2-1}(\kappa)$ is the modified Bessel function of the first kind.

Therefore, to measure the density of training examples around a given point, p(s) can be computed using the above equations. This gives an idea of how familiar the model is with the region around a given embedding.

A novel metric, herein referred to as the density consistency (DC) can be designed to assess the preservation of density consistency between the input data and the model's output embeddings. The DC is a measure of a model's ability to maintain the structural and relational characteristics of the data in its transformation to the embedding space. Density consistency is shown in FIG. 1, Step 3 (part I).

Given a data point x and its embedding s the DC is mathematically formulated as follows:

$$DC = |D_i(x) - D_e(s)|$$

In this formula, $D_i(x)$ is the density of the input data around a given point x, which is estimated using domain-specific knowledge, and $D_e(s)$ is the density of the embeddings around a given point s, which is estimated using the von Mises-Fisher Mixture Model (vMFMM) as outlined above. The absolute value of the difference between these two densities yields the DC. In the case of MS/MS spectra, the density of the input data $D_i(x)$ is calculated using the cosine similarity metric. This serves to gauge the similarity between pairs of input spectra. This metric, therefore, allows for quantitative evaluation of the model's performance in terms of its ability to maintain the integrity of data relationships and structure in the transformation from the input space to the embedding space. The lower the value of DC, the more effectively the model preserves the original data structure in its output embeddings.

Embodiments of the subject invention provide a focused technical solution to the focused technical problem of how to predict peptide properties from MS data before any deduction (i.e., directly from MS data, and/or before any database search). The solution is provided by utilizing a novel attention and multitask deep network that can predict multiple peptide properties (e.g., length, missed cleavages, and/or modification status) directly from MS data with very high accuracy (e.g., at least 90%, such as at least 95% or at least 97%). Embodiments of the subject invention can improve the computer system predicting peptide properties by efficiently performing the prediction directly from MS data without the need for any deduction, database search, or modification of the data (this can free up memory and/or processor usage). The predicted properties can be used in many practical applications, including but not limited to: providing to scientists, clinicians, and/or health care professionals new filters for database search of peptides (embodiments of the subject invention include providing the new filter(s), based on the predicted peptide properties, as well as the scientists, clinicians, and/or health care professionals performing a database search using the new filter(s)); using the predicted peptide properties in clinical proteomics, such as performing qualitative profiling of proteins and peptides that are present in clinical specimens like tissues and body fluids (embodiments of the subject invention include providing the predicted peptide properties to scientists, clinicians, and/or health care professionals, as well as using the predicted peptide properties in the clinical proteomics); and diagnosing diseases that can specifically be diagnosed on the basis of proteomics and/or peptide properties (embodiments of the subject invention include providing the predicted peptide properties to scientists, clinicians, and/or health care professionals, as well as using the predicted peptide properties to diagnose such diseases).

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When the term module is used herein, it can refer to software and/or one or more algorithms to perform the function of the module; alternatively, the term module can refer to a physical device configured to perform the function of the module (e.g., by having software and/or one or more algorithms stored thereon).

When ranges are used herein, combinations and subcombinations of ranges (including any value or subrange contained therein) are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

Pride Archive (PXD) datasets were constructed for experimentation and evaluation for proteomics search: PXD000612 (see also Sharma et al., Ultradeep human phosphoproteome reveals a distinct regulatory nature of tyr and ser/thr-based 512 signaling, Cell reports, 8(5):1583-1594, 2014; which is hereby incorporated by reference herein in its entirety), PXD001468 (see also Chick et al., A mass-tolerant database search identifies a large proportion of unassigned spectra in shotgun proteomics as modified peptides, Nature biotechnology, 33(7):743-749, 2015; which is hereby incorporated by reference herein in its entirety), and PXD009861 (see also Bittremieux et al., Fast open modification spectral library searching through approximate nearest neighbor indexing, Journal of proteome research, 17(10): 3463-3474, 518 2018; which is hereby incorporated by reference herein in its entirety). When extending the experiments to meta-proteomics database searches, the RefUP++ database was used, encompassing 2,259 genera (see also Beyter, supra.). In order to gain insights into the predictive models, experiments were performed for three distinct sets. The first set of experiments were performed for evaluating the results of the predictive model (i.e. how accurate is the ProteoRift model when trying to predict the length, missed cleavages, and modifications). The second set of experiments were performed for the database search that is batched according to the model predictions. This set of experiments informs about the performance of the end-to-end pipeline as compared to related art algorithmic techniques. Further, these experiments inform about the potential search-space and processing time reduction. The last set of experiments were completed to assess the confidence of the ML database search embedding, and inform us about the confidence metrics when compared with the ground truth data sets.

The experiments are performed using the PyTorch framework 1.13.0 and Python 3.10.8. For fast training, NVIDIA V100s (32 GB SMX2) GPUs were utilized with 32 GB of memory provided by Expanse SDSC supercomputer installed in nodes with up to 4 GPU nodes, 40 CPU cores, and 384 GBs of memory (10 CPU cores and 96 GBs per GPU node). In addition, NVIDIA A6000 GPUs with 48 GBs of memory were utilized as part of the in-house cluster (dragon).

The model was trained using high-quality spectra with selected label peptides. Three datasets were used—NIST (see also Nist libraries of peptide tandem mass spectra, chemdata.nist.gov/dokuwiki/doku.php?id=peptidew:start; which is hereby incorporated by reference herein in its entirety), MassIVE (see also Massive-kb peptide spectral libraries, massive.ucsd.edu/ProteoSAFe/static/massive-kb-libraries.jsp; which is hereby incorporated by reference herein in its entirety), and DeepNovo (see also Tran et al., De novo peptide sequencing by deep learning, Proceedings of the National Academy of Sciences, 114(31):8247-8252, 2017; which is hereby incorporated by reference herein in its entirety). The spectral libraries were preprocessed to extract the MS/MS spectra along with the target labels from the corresponding peptide (i.e., peptide sequence length, missed cleavages, and modification status). Peptide sequence length was calculated as the number of amino acids in the peptide regardless of the modifications on any amino acid. Missed cleavages were calculated as the number of K and R amino acids within the sequence except if followed by P or when at the end of the peptide sequence. Modification status was calculated as true or false depending on whether there was a dynamic modification (one or more) on any number of amino acids. Carbamidomethylation (CAM) on amino acid C was not considered a modification for the data. About 2.7 million (M) spectra were obtained with known peptide labels, out of which about 0.37 M were modified, and the rest were unmodified. The dataset contained about 1.7 M spectra with 2+ precursor charge and about 0.5 M spectra with 3+ precursor charge. In terms of missed cleavages, the training dataset contained about 2 M, about 0.7 M, and about 50,000 spectra with zero, one, and two missed cleavages, respectively. Train/Validation/Test split of 0.7/0.2/0.1 was used for training the network and tuning hyperparameters. Now, the dataset only contained oxidation modifications. The precursor charge value of the spectra was restricted to a maximum of 3+. The distribution of length missed cleavages, and modification status is shown in FIG. 8.

Example 1

On the test dataset, the precision values of all classes were measured for each head. The model predicted the length with high precision for smaller lengths, which then gradually dropped for large length values (see FIG. 2, top left). This is to be expected because of limited data available to train the models for larger length peptides. The fact that the total precision value of greater than 90% was observed for most lengths within ±1 demonstrates that the head is sufficiently trained and predicts lengths with high precision. In light of these results, it was considered that the predicted_length=actual_length±1 (i.e., Len+/−1) to be accurate for any subsequent experiments and the model.

Figure 2:
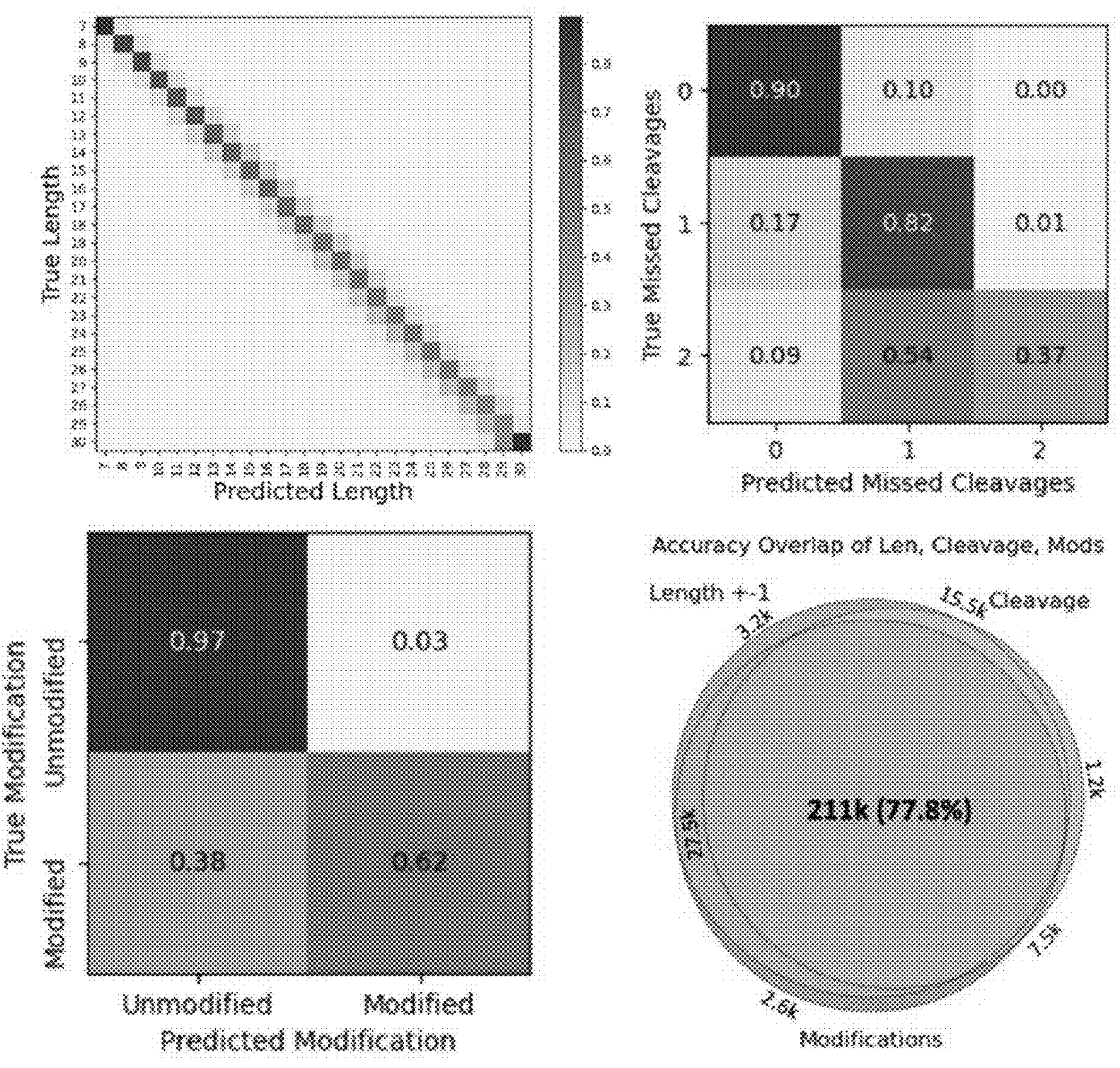
FIG. 2 shows a confusion matrix of peptide length missed cleavages, and modification status predictions. For length prediction, precision is high for smaller lengths and gradually drops for larger length values, because a smaller number of training samples are available at larger lengths (similar to in real-life mass spectrometry (MS) experiments). When peptides within ±1 of the predicted length are considered, precision value is >90% for most lengths. The illustrated Venn diagram (lower right of FIG. 2) depicts the correct predictions of all three heads. The systems and methods of embodiments of the subject invention (which can be referred to herein as "ProteoRift") accurately predict all three properties 77.8% of the time. For length prediction, the recommended error tolerance of ±1 was used for optimal performance.

The experiments also demonstrated that head to predict cleavage also worked with high precision (see FIG. 2, top right). As shown in FIG. 2, the 0 and 1 missed cleavages were predicted with 90% and 82% accuracy, respectively. However, the precision dropped rapidly for 2 missed cleavages. This is again to be expected because 2 missed cleavages are rare in real-world data, which is also apparent in the training data sets. For the experiments, it was ensured that the peptide database was generated with an equal portion of 2 missed cleavage peptides, and therefore the effective precision in real-world setting would be much higher providing considerable benefit in terms of reducing search space.

The model predicts with exceptional performance of more than 97% precision for unmodified spectra as shown in FIG. 2 (bottom left). While the performance for the much more difficult problem of modification status is close to 62%, it is much better than random chance and will result in reduction in the search-space. This behavior is also expected because the number of modifications is a very large in number, leading to explosion in possible modification patterns in the spectra. While the model did learn, and performed better than random for modification status on unseen data, more data may lead to better performance.

The average performance of three heads will determine the accuracy of the overall predictive model and its effect on the search-space. The aggregate performance evaluation of the model was performed by measuring the total number of correct measurements for all heads. As shown in FIG. 2 (bottom right), the model was able to accurately predict all three properties 77.8% of the time.

Example 2

A set of experiments was completed to estimate the effect of the filters on the search-space as well as the accuracy of the peptides deduced using the modified search-space. For the predictive filtering to be effective, the peptide deductions on modified search-spaces must be at par with other algorithmic techniques. In order to perform comprehensive evaluation of the effect of the predictive filtering on peptide deduction quality and execution time, various permutations of the filter were incorporated. This predictive filter configuration includes: 1) applying all filters simultaneously; 2) selectively applying missed cleavages and modification filters; and (3) implementing all filters in conjunction with a relaxed length filter with a margin of ±1.

Figure 3A:
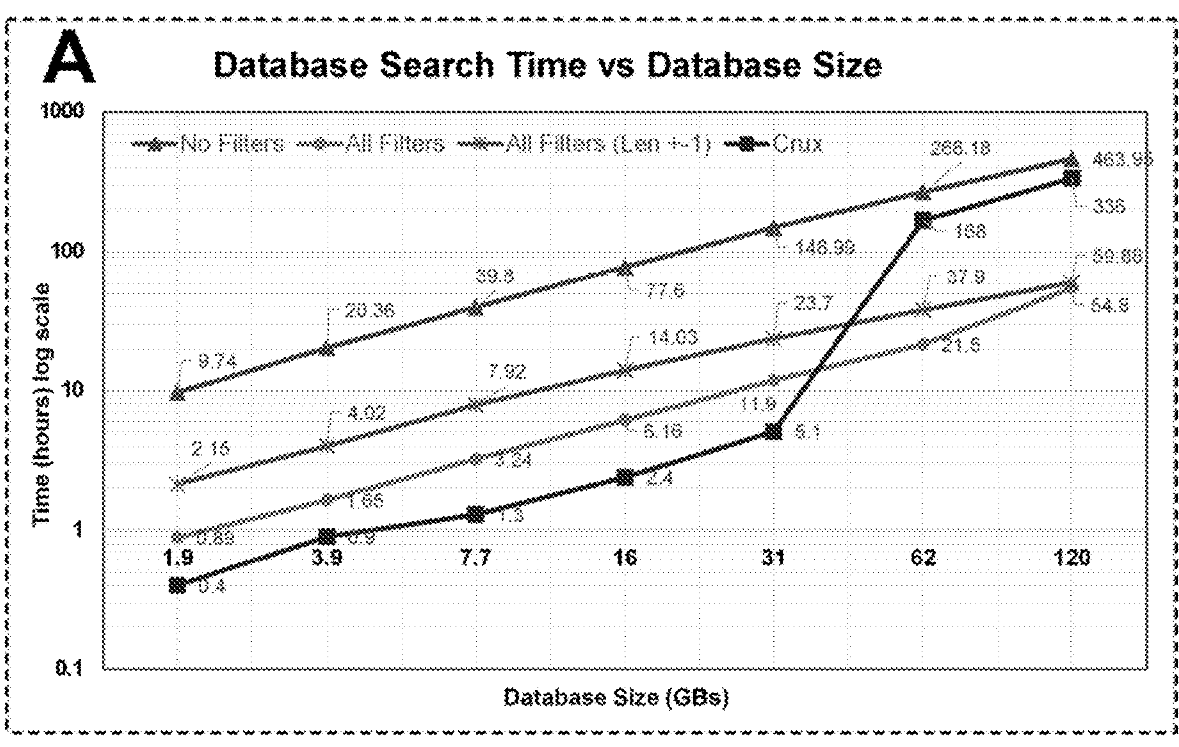
FIG. 3A shows a plot of time of execution (in hours, log scale) versus database size (in gigabytes (GBs)) at different filter configurations, for a meta-proteomics database. The curve with the triangular data points and the highest time values is for no filters; the curve with the * datapoints and the second-highest time value at the lowest database size value is for all filters (Len+/−1); the curve with the circular datapoints and the third-highest time value at the lowest database size value is for all filters; and the curve with the square datapoints and the lowest time value at the lowest database size value is for Crux. The search was performed against a meta-proteomics database published by Proteostorm (RefUP++ database; Beyter et al., Proteostorm: An ultrafast metaproteomics database search framework, Cell systems, 7(4):463-467, 2018; which is hereby incorporated by reference herein in its entirety). The mass spectra from the msv000082031 spectral dataset was used.
Figure 3B:
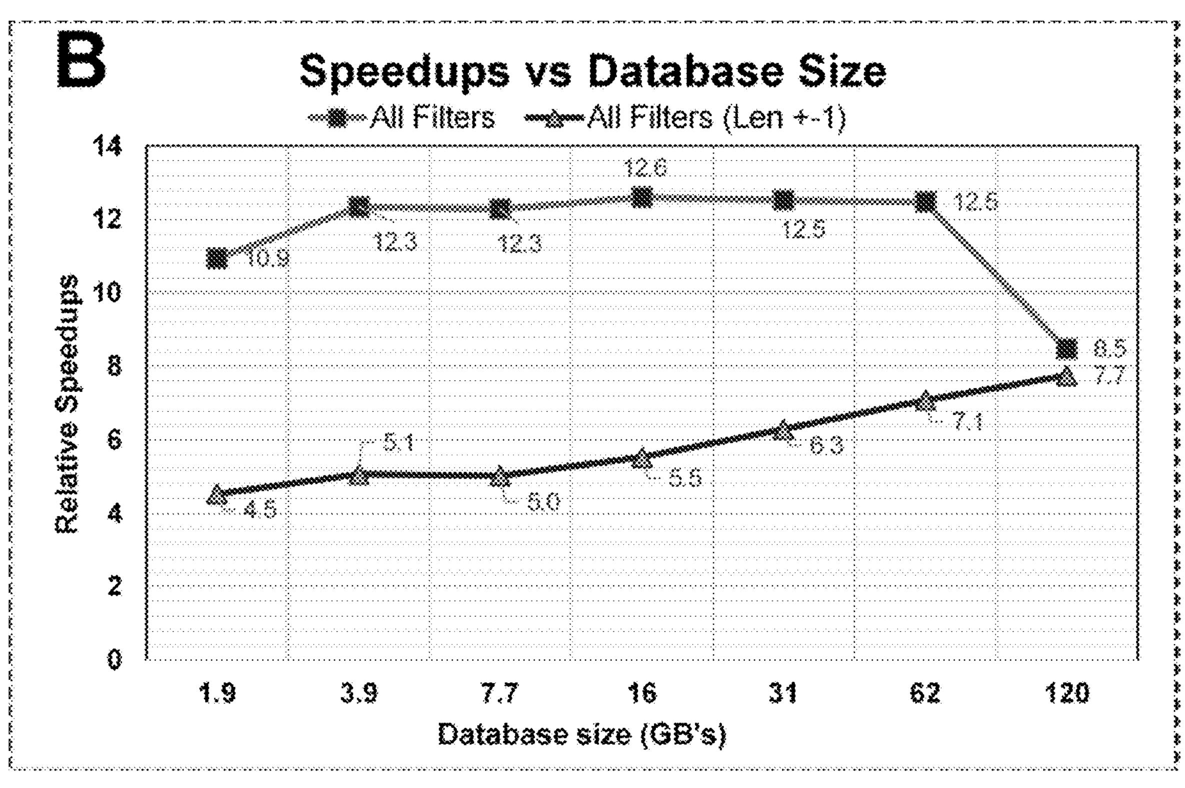
FIG. 3B shows a plot of time of relative speedups versus database size (in GBs) at different filter configurations, for a meta-proteomics database. The curve with the triangular data points and the lowest number of relative speedups is for all filters (Len+/−1); and the curve with the square datapoints and the highest number of relative speedups is for all filters. The search was performed against a meta-proteomics database published by Proteostorm (RefUP++ database; Beyter et al., supra.). The mass spectra from the msv000082031 spectral dataset was used. When all filters were applied, up to 12× speedup was obtained while 8× speedup was obtained when enabling the length error margin of ±1.

The first thing to establish was if predictive filtering effectively reduced the search-space when deducing peptide from database-search. The search was performed against a meta-proteomics database published by Proteostorm (see also Beyter, supra.). The mass spectra used were from the msv000082031 spectral dataset. For the meta-proteomics search experiments, the database size varied from 2 gigabytes (GB) to 120 GB. As shown in FIGS. 3A and 3B, the speedup after using filters increased gradually as the database size increased. This is likely due to the reduced number of out-of-core computations when additional filters are applied leading to a more optimal memory access pattern. Crux, which is a highly optimized piece of code, was better than the unoptimized search-code, the advantage disappeared as the size of the database increased. For any optimized code, better speedups than are reported here would be expected. In general, the experiments demonstrated that when all filters are applied, 8× to 12× speedups were obtained. Speedups of up to 7.7× were obtained when enabling the length error margin of ±1. This is predominantly attributed to a significant reduction in out-of-core computations, a frequent computational bottleneck in large-scale database searches. Because predictive filtering does result in smaller search-space and better execution times especially for larger databases, the peptide deduction results were next compared with existing state-of-the-art algorithmic techniques.

Figure 3C:
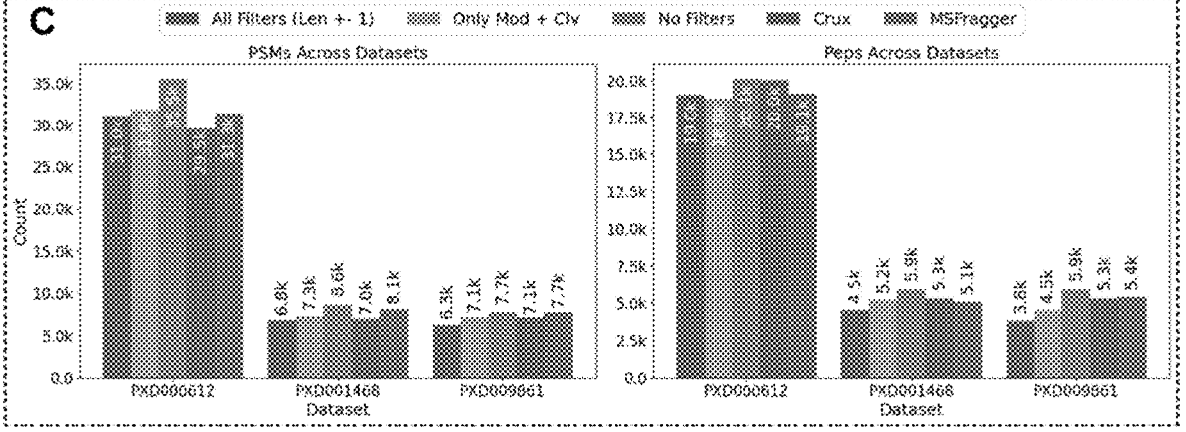
FIG. 3C shows a comparison of the number of peptide-spectrum matches (PSMs) (left bar chart) and peptides (right bar chart) identified under 1% false discovery rate (FDR) against SpeCollate with a length filter. Within each dataset in the bar charts, the left-most bar is for all filters (LEN+/−1), the second-from-the-left bar is for only Mod+Civ, the middle bar is for no filters, the second-from-the-right bar is for Crux, and the right-most bar is for MSFragger.
Figure 3D:
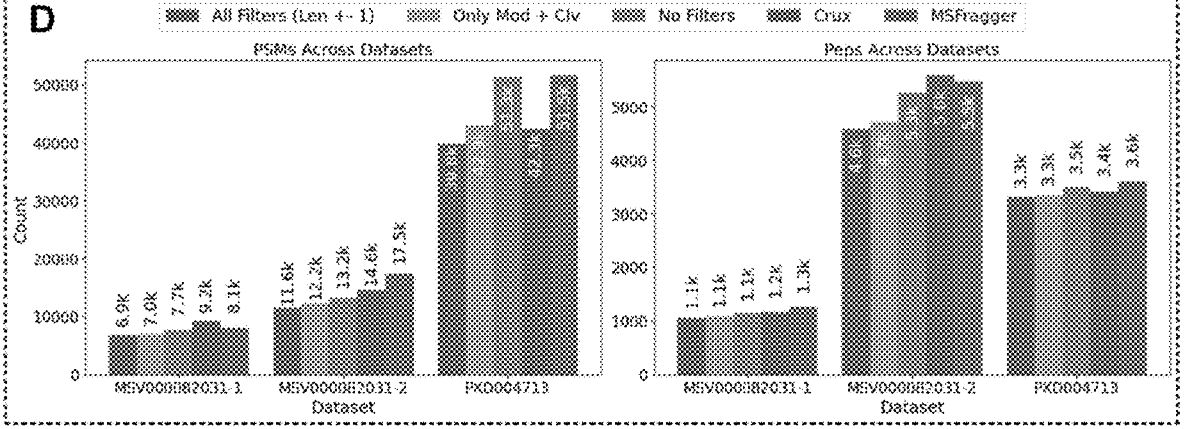
FIG. 3D shows a comparison of the number of PSMs (left bar chart) and peptides (right bar chart) identified under 1% FDR against SpeCollate without a length filter. Within each dataset in the bar charts, the left-most bar is for all filters (LEN+/−1), the second-from-the-left bar is for only Mod+Civ, the middle bar is for no filters, the second-from-the-right bar is for Crux, and the right-most bar is for MSFragger.

Because a predictive filtering model can be used with any database search-engine, its effectiveness when deployed for proteomics experiments was assessed. For varying filter configurations three distinct datasets were evaluated (PXD000612, PXD001468, and PXD009861). In these trials, two primary metrics were considered: the number of identified peptides under a 1% false discovery rate (FDR); and the resulting speedup of the database search process. As shown in FIG. 3C, the peptide-spectrum match (PSM) results with no-filter (Specollate) was better than both Crux and MSFragger for PXD000612 and PXD001468 and comparable to MSFragger for PXD009861. For PXD000612, the mod+leavage filter performed better than both Crux and MSFragger for PSM and performed comparably for the other two datasets. When all filters were used, which is arguably the most stringent settings, the PSM identified were still comparable while giving 8× to 12× speedups as compared to non-filtered settings. The number of peptides identified when using the mod+cleavage filter was comparable to MSFragger and Crux for all data sets.

When extending the experiments to meta-proteomics database searches, the RefUP++ database was used, encompassing 2,259 genera. The number of peptides identified (at 1% FDR) were analyzed with different configurations for the meta-proteomics database. The results shown in FIG. 3D demonstrate that the number of PSMs and peptides identified are comparable to MSFragger and Crux for msv000082031-1, msv000082031-2, and PXD004713. For PXD004713 the number of PSMs using a filtering technique surpassed Crux when only modification and cleavage predictive filtering was used. While the number of PSMs is higher for MSFragger, the number of unique peptides identified are comparable when predictive filtering is used. Last, the results are extremely encouraging considering that the number of peptides identified with filtered subsets is comparable to when no filter is applied, highlighting that the predictive filters of embodiments of the subject invention can provide significant speedup while having a negligible effect on result quality, all while exhibiting an speedup (e.g., 12× speedup). This improvement is a vast advancement over the speedup obtained by solely applying the precursor mass filter, further illustrating the value of predictive filtering.

Example 3

In order to determine how well the metrics estimate aleatoric uncertainty for a given embedding, an MS dataset that is similar to SpeCollate's training data can be used, i.e., ProteomeTools HCD data (see also, Spectral libraries, proteometools.org/index.php?id=53; which is hereby incorporated by reference herein in its entirety). This can be considered to see how well these metrics can predict the downstream performance of the in-distribution embeddings (e.g., how well the mass spectra embeddings can be identified in a peptide database search). Ideally, higher confidence along with a higher ranking of the spectrum would indicate the model is certain about its decision. To quantify this, peptide embeddings can be ranked from the human peptide database against each spectrum. A true label can be assigned to a spectrum if the correct peptide is ranked the highest. The label definition is given below:

$$\text{Label} = \begin{cases} 1 & \text{correct peptide is ranked highest,} \\ 0 & \text{otherwise.} \end{cases}$$

A gradient-boosting decision tree (GBDT) model can be trained with per-sample feature variations (variations for short), density, and density consistency as input and the above-described labels as output. Hyperparameter tuning can be performed for the max depth, learning rate, and number of estimators. The optimal values selected are shown in the table in FIG. 12.

Detailed analysis of the metrics performance is given in the table in FIG. 10. As can be seen in the table in FIG. 10, the per-sample feature variation (variation) metric yielded a promising ROC-AUC score of 0.84, surpassing the other individual metrics. This finding illustrates that the model's confidence in an example's embedding position is a crucial indicator for identifying high-quality spectra. Combining the variations and density metrics resulted in a significant enhancement in all performance metrics emphasizing that the two metrics combined capture different aspects of uncertainty providing overall better performance in retrieving high-quality examples. The combination of all three metrics yielded the best performance across all metrics, with a ROC-AUC score of 0.94. This reveals that a holistic view, encompassing variations in embedding, data distribution around the embedding, and consistency between input and embedding densities, provides the most potent approach for identifying high-quality spectra.

To estimate epistemic uncertainty, in-distribution and out-of-distribution data points can be classified using the uncertainty metrics. For in-distribution and out-of-distribution data, ProteomeTools HCD and CID datasets were used. As SpeCollate is solely trained on HCD data, CID data is an obvious choice for out-of-distribution examples to validate the uncertainty metrics. The following labels were assigned to the curated dataset with nearly 1 million examples for each class:

$$\text{Label} = \begin{cases} 1 & \text{Id-distribution data point,} \\ 0 & \text{Out-of-distribution data point.} \end{cases}$$

A GBDT model was trained on this data with a 70-20-10 split of train validation and test subsets. The optimal parameters selected after hyperparameter tuning are given in the table shown in FIG. 13.

The standout performance of the consistency metric (ROC-AUC of 0.99) reinforces its innovative design. Assessing the alignment between the density of input data, and embeddings offers insight into the consistency of the model's behavior, providing a crucial aspect of uncertainty evaluation. Detailed results are given in the table shown in FIG. 11.

Figure 4:
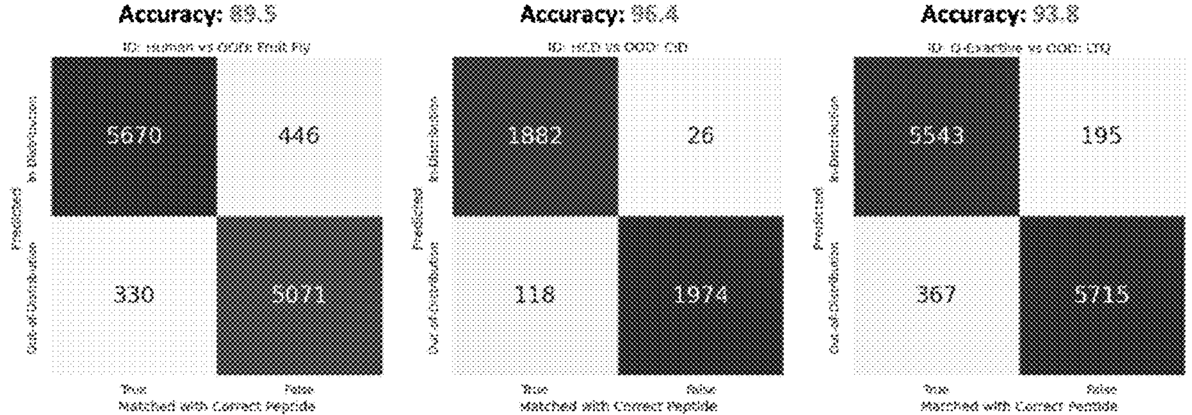
FIG. 4 shows peptide identification accuracy of spectra predicted in-distribution versus out-of-distribution. Three different combinations of in-distribution and out-of-distribution datasets were used to compare the downstream performance with the predicted accuracy. For Human versus Fruitfly, datasets PXD009861 and PXD030281 were used. For higher-energy collisional dissociation (HCD) versus collision-induced dissociation (CID), ProteomeTools HCD and CID libraries were used. For Q-Exactive vs linear trap quadrupole (LTQ), datasets PXD000612 and PXD000125 were used.

In order to further validate the results, a database search on both in-distribution and out-of-distribution datasets was performed. Three datasets were selected, where each dataset is a mixture of in-distribution and out-of-distribution data. Confusion matrices were calculated to determine what percentage of in-distribution predicted spectra matched with the correct peptide. As shown in FIG. 4, the predicted in-distribution data points performed vastly better than the predicted out-of-distribution data, with an accuracy of up to 96.4%.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for predicting properties of peptides from mass spectrometry (MS) data of the peptides, the system comprising:

a processor; and a machine-readable medium in operable communication with the processor and having instructions stored thereon that, when executed by the processor, perform the following steps:

i) receiving the MS data as input;

ii) capturing sequence dependencies in the MS data;

iii) generating an intermediate output using the sequence dependencies;

iv) combining a feature vector of mass and charge values with the intermediate output to generate a combined feature vector;

v) generating spectrum embeddings using the combined feature vector;

vi) predicting the properties of the peptides based on the spectrum embeddings;

vii) using the predicted properties of the peptides to diagnose a disease;

viii) generating peptide embeddings from the peptides using two bidirectional long short-term memory networks;

ix) estimating a confidence of the spectrum embeddings by ranking the peptide embeddings against the spectrum embeddings;

x) determining a certainty of embedding location by introducing controlled augmentations to the MS data and measuring a variation in the spectrum embeddings;

xi) measuring a training data density around spectrum embedding using a von Mises-Fisher Mixture Model; and xii) evaluating whether a first density of the MS data is consistent with a second density of the spectrum embeddings, the properties of the peptides being predicted directly from the MS data without any prior deduction or database search on the MS data.

2. The system according to claim 1, the MS data comprising at least one of mass to charge ratio (m/z), intensity, and index value.

3. The system according to claim 1, the MS data comprising mass to charge ratio (m/z), intensity, and index value.

4. The system according to claim 1, the properties of the peptides comprising at least one of length, missed cleavages, and modification status.

5. The system according to claim 1, the properties of the peptides comprising length, missed cleavages, and modification status.

6. The system according to claim 1, the capturing of the sequence dependencies in the MS data comprising using two 8-headed self-attention layers.

7. The system according to claim 1, the predicting the properties of the peptides based on the spectrum embeddings comprising sending the spectrum embeddings through a first branch of two fully connected layers to predict a first property of the peptides, a second branch of two fully connected layers to predict a second property of the peptides, and a third branch of two fully connected layers to predict a third property of the peptides.

8. The system according to claim 1, the generating an intermediate output using the sequence dependencies comprising sending the sequence dependencies through two fully connected layers to generate the intermediate output.

9. A method for predicting properties of peptides from mass spectrometry (MS) data of the peptides, the method comprising:

i) receiving the MS data as input;

ii) capturing sequence dependencies in the MS data;

iii) generating an intermediate output using the sequence dependencies;

iv) combining a feature vector of mass and charge values with the intermediate output to generate a combined feature vector;

v) generating spectrum embeddings using the combined feature vector;

vi) predicting the properties of the peptides based on the spectrum embeddings;

vii) using the predicted properties of the peptides to diagnose a disease;

viii) generating peptide embeddings from the peptides using two bidirectional long short-term memory networks;

ix) estimating a confidence of the spectrum embeddings by ranking the peptide embeddings against the spectrum embeddings;

x) determining a certainty of embedding location by introducing controlled augmentations to the MS data and measuring a variation in the spectrum embeddings;

xi) measuring a training data density around spectrum embedding using a von Mises-Fisher Mixture Model; and xii) evaluating whether a first density of the MS data is consistent with a second density of the spectrum embeddings, the properties of the peptides being predicted directly from the MS data without any prior deduction or database search on the MS data.

10. The method according to claim 9, the MS data comprising at least one of mass to charge ratio (m/z), intensity, and index value.

11. The method according to claim 9, the MS data comprising mass to charge ratio (m/z), intensity, and index value.

12. The method according to claim 9, the properties of the peptides comprising at least one of length, missed cleavages, and modification status.

13. The method according to claim 9, the properties of the peptides comprising length, missed cleavages, and modification status.

14. The method according to claim 9, the capturing of the sequence dependencies in the MS data comprising using two 8-headed self-attention layers.

15. The method according to claim 9, the predicting the properties of the peptides based on the spectrum embeddings comprising sending the spectrum embeddings through a first branch of two fully connected layers to predict a first property of the peptides, a second branch of two fully connected layers to predict a second property of the peptides, and a third branch of two fully connected layers to predict a third property of the peptides.

16. The method according to claim 9, the generating an intermediate output using the sequence dependencies comprising sending the sequence dependencies through two fully connected layers to generate the intermediate output.

17. A system for predicting properties of peptides from mass spectrometry (MS) data of the peptides, the system comprising:

a processor;

a display in operable communication with the processor; and a machine-readable medium in operable communication with the processor and the display and having instructions stored thereon that, when executed by the processor, perform the following steps:

i) receiving the MS data as input;

ii) capturing sequence dependencies in the MS data;

iii) generating an intermediate output using the sequence dependencies;

iv) combining a feature vector of mass and charge values with the intermediate output to generate a combined feature vector;

v) generating spectrum embeddings using the combined feature vector;

vi) predicting the properties of the peptides based on the spectrum embeddings; and vii) using the predicted properties of the peptides to diagnose a disease;

viii) generating peptide embeddings from the peptides using two bidirectional long short-term memory networks;

ix) estimating a confidence of the spectrum embeddings by ranking the peptide embeddings against the spectrum embeddings;

x) determining a certainty of embedding location by introducing controlled augmentations to the MS data and measuring a variation in the spectrum embeddings;

xi) measuring a training data density around spectrum embedding using a von Mises-Fisher Mixture Model; and xii) evaluating whether a first density of the MS data is consistent with a second density of the spectrum embeddings, the properties of the peptides being predicted directly from the MS data without any prior deduction or database search on the MS data, the MS data comprising mass to charge ratio (m/z), intensity, and index value, the properties of the peptides comprising length, missed cleavages, and modification status, the capturing of the sequence dependencies in the MS data comprising using two 8-headed self-attention layers, the predicting the properties of the peptides based on the spectrum embeddings comprising sending the spectrum embeddings through a first branch of two fully connected layers to predict a first property of the peptides, a second branch of two fully connected layers to predict a second property of the peptides, and a third branch of two fully connected layers to predict a third property of the peptides, and the generating an intermediate output using the sequence dependencies comprising sending the sequence dependencies through two fully connected layers to generate the intermediate output.

* * * * *